(12) United States Patent
Malergue et al.

(10) Patent No.: US 11,635,433 B2
(45) Date of Patent: *Apr. 25, 2023

(54) METHOD FOR LABELING INTRACELLULAR AND EXTRACELLULAR TARGETS OF LEUKOCYTES

(71) Applicant: BECKMAN COULTER, INC., Brea, CA (US)

(72) Inventors: Fabrice Malergue, Marseilles (FR); Andreas Van Agthoven, Marseilles (FR)

(73) Assignee: Beckman Coulter, Inc., Brea, CA (US)

( * ) Notice: Subject to any disclaimer, the term of this patent is extended or adjusted under 35 U.S.C. 154(b) by 413 days.

This patent is subject to a terminal disclaimer.

(21) Appl. No.: 15/188,856

(22) Filed: Jun. 21, 2016

(65) Prior Publication Data

US 2016/0299139 A1    Oct. 13, 2016

Related U.S. Application Data

(63) Continuation of application No. 14/366,024, filed as application No. PCT/IB2012/003071 on Dec. 21, 2012, now Pat. No. 9,678,073.

(30) Foreign Application Priority Data

Dec. 21, 2011   (EP) ..................................... 11290586

(51) Int. Cl.
*G01N 33/569*   (2006.01)
*G01N 1/30*     (2006.01)

(52) U.S. Cl.
CPC ......... *G01N 33/56972* (2013.01); *G01N 1/30* (2013.01)

(58) Field of Classification Search
CPC .............. G01N 33/56972; G01N 1/30; G01N 2001/302; G01N 33/5094
See application file for complete search history.

(56) References Cited

U.S. PATENT DOCUMENTS

| | | | |
|---|---|---|---|
| 7,678,578 B2 * | 3/2010 | Van Agthoven | A61K 31/198 436/17 |
| 9,678,073 B2 | 6/2017 | Malergue et al. | |
| 2001/0031482 A1 * | 10/2001 | James | G01N 1/30 435/40.5 |
| 2004/0229368 A1 | 11/2004 | Maples et al. | |
| 2005/0266503 A1 | 12/2005 | Purvis et al. | |
| 2006/0046272 A1 | 3/2006 | Chow et al. | |
| 2007/0072247 A1 | 3/2007 | Wong et al. | |
| 2015/0010923 A1 | 1/2015 | Malergue et al. | |

FOREIGN PATENT DOCUMENTS

| | | |
|---|---|---|
| EP | 0562877 | 9/1993 |
| EP | 2607899 A1 | 6/2013 |
| EP | 2607899 B1 | 8/2016 |
| WO | WO-2013093642 A1 | 6/2013 |

OTHER PUBLICATIONS

Caldwell et al., "Preservation of B-cell-associated surface antigens by chemical fixation", Cytometry, vol. 16, No. 3, Jul. 1, 1994, pp. 243-249.

Giloh , "Analysis of intracellular antigens by flow cytometry: methods for cell permeabilization to antibodies", Flow Cytometry, 1993, vol. 67, pp. 65-101.

Jacobberger et al., "Intracellular antigen staining," Methods: A Companion to Methods in Enzymology, 1991, vol. 2, No. 3, pp. 207-218.

Lntraprep , https://www.bc-cytometry.com/PDF/DataSheet/A07802.pdf, 2006, 3 pages.

Shankey et al., "An optimized whole blood method for flow cytometric measurement of ZAP-70 protein expression in chronic lymphocytic leukemia", Cytometry Part B, vol. 70B, No. 4, Jul. 15, 2006, pp. 259-269.

International Search Report and Written Opinion dated Jun. 3, 2013 for PCT Patent Application No. PCT/IB2012/003071, 10 pages.

"U.S. Appl. No. 14/366,024, Amendment filed Mar. 2, 2017", 7 pgs.

"U.S. Appl. No. 14/366,024, Non Final Office Action dated Feb. 23, 2016", 16 pgs.

"U.S. Appl. No. 14/366,024, Notice of Allowance dated Mar. 14, 2017", 10 pgs.

"U.S. Appl. No. 14/366,024, Notice of Non-Compliant Amendment dated Oct. 18, 2016", 5 pgs.

"U.S. Appl. No. 14/366,024, Preliminary Amendment filed Jun. 17, 2014", 8 pgs.

"U.S. Appl. No. 14/366,024, Response filed May 19, 2016 to Non Final Office Action dated Feb. 23, 2016", 12 pgs.

"U.S. Appl. No. 14/366,024, Response filed Oct. 13, 2015 to Restriction Requirement dated Aug. 12, 2015", 9 pgs.

"U.S. Appl. No. 14/366,024, Response filed Dec. 5, 2016 to Notice of Non-Compliant Amendment dated Oct. 18, 2016", 8 pgs.

"U.S. Appl. No. 14/366,024, Restriction Requirement dated Aug. 12, 2015", 13 pgs.

(Continued)

*Primary Examiner* — Gailene Gabel

(74) *Attorney, Agent, or Firm* — Schwesman Lundberg & Woessner, P.A.

(57) ABSTRACT

The present invention relates to methods for labeling intracellular and extracellular targets of leukocytes, as well as to kits for performing said methods.

15 Claims, 3 Drawing Sheets

(56) References Cited

OTHER PUBLICATIONS

"European Application Serial No. 11290586.4, Communication Pursuant to Article 94(3) EPC dated Mar. 27, 2014", 5 pgs.
"European Application Serial No. 11290586.4, Communication Pursuant to Article 94(3) EPC dated Jul. 24, 2013", 5 pgs.
"European Application Serial No. 11290586.4, Extended European Search Report dated Jun. 25, 2012", 7 pgs.
"European Application Serial No. 11290586.4, Intention to Grant dated Feb. 19, 2016", 24 pgs.
"European Application Serial No. 11290586.4, Office Action dated Jun. 30, 2015", 4 pgs.
"European Application Serial No. 11290586.4, Response filed Jul. 21, 2014 to Communication Pursuant to Article 94(3) EPC dated Mar. 27, 2014", 21 pgs.
"European Application Serial No. 11290586.4, Response filed Oct. 30, 2015 to Office Action dated Jun. 30, 2015", 22 pgs.
"European Application Serial No. 11290586.4, Response filed Nov. 15, 2012 to Extended European Search Report dated Jun. 25, 2012", 21 pgs.
"European Application Serial No. 11290586.4, Response filed Nov. 21, 2013 to Communication Pursuant to Article 94(3) EPC dated Jul. 24, 2013", 11 pgs.
"International Application Serial No. PCT/IB2012/003071, International Preliminary Report on Patentability dated Jul. 3, 2014", 6 pgs.

* cited by examiner

METHOD FOR LABELING INTRACELLULAR AND EXTRACELLULAR TARGETS OF LEUKOCYTES

CROSS-REFERENCES TO RELATED APPLICATIONS

This application is a continuation of U.S. patent application Ser. No. 14/366,024 filed on Jun. 17, 2014, which is a National Stage Application of PCT/IB2012/003071, filed Dec. 21, 2012, which claims benefit of European Application No. 11290586.4, filed Dec. 21, 2011, the disclosures of which application are incorporated herein by reference.

DESCRIPTION

The present invention relates to methods for labeling intracellular and extracellular targets of leukocytes, as well as to kits for performing said methods.

The staining of leukocytes with binding agents such as monoclonal antibodies (mAbs) is an important task that is routinely performed both in basic research as well as in a variety of diagnostic applications. Very often, extracellular as well as intracellular markers of the leukocytes have to be stained, e.g. in order to identify a particular subset of leukocytes by specific extracellular surface markers, as well as functional characteristics of the cells by specific molecules that are present in the cytoplasma.

In order to stain leukocytes intracellularly with e.g. mAbs and to render them analyzable by flow cytometry, it is necessary to permeabilize the leukocytes and lyse red blood cells that are present in the sample while maintaining the native state of the structures of the leukocytes, both at the cell surface and inside the cell, to which the binding agents should bind. This goal is commonly achieved by the use of detergents and/or alcohols. Following a fixation step using e.g. formaldehyde or alcohols, red blood cells are less resistant to detergents than leukocytes, allowing the lysis of the red blood cells and the analysis of permeabilized leukocytes.

Many methods for the extra- and intracellular staining of leukocytes are based on the same principle. In particular, the surface markers of the cells are stained first, followed by one ore more washing step(s) (i.e. centrifuging the cells, discarding the supernatant, and then resuspending them in fresh buffer), in order to remove any unbound binding agent. Then, the cells are fixed, again followed by one or more washing steps to remove the fixative, permeabilized, washed again, then stained with the intracellular binding agents and finally washed again.

However, these procedures are not only time consuming, with a total duration of up to 2 to 3 hours, but also quite labor intensive. Further, there are at least two mandatory centrifugation steps, rendering an automation of the procedure almost impossible. Furthermore, centrifugation can be detrimental to the structure of the cells, thus worsening the light scatter signals of the cells as compared to cells that have not been centrifuged. Moreover, centrifugation always leads to a loss of cells and to cell clumping. Finally, extra- and intracellular binding agents must be used and applied separately, prohibiting the convenient use of a binding agent cocktail.

Therefore, the technical problem underlying the present invention is to provide an improved method for the labeling of intracellular and extracellular targets of leukocytes that is fast and not very labor intensive, does avoid any centrifugation steps, allows the use of binding agent cocktails and can be easily automated.

The solution to the above technical problem is achieved by the embodiments characterized in the claims.

In particular, the present invention relates to a method for labeling intracellular and extracellular targets of leukocytes, comprising the steps of:
(a) forming a combination of
   (i) a cellular composition, comprising at least leukocytes and red blood cells, and
   (ii) a first solution comprising one or more agent(s) that are capable of cross-linking intracellular proteins, lipoproteins and nucleic acids of said leukocytes;
(b) adding a second solution to said combination, comprising one or more agent(s) that are capable of permeabilizing said leukocytes, lysing said red blood cells and neutralizing the cross-linking activity of said one or more agent(s) in said first solution,
   characterized in that the added volume of said second solution is between 1 and 10 times the total volume of said combination;
(c) adding either concurrently with or subsequently to addition of said second solution at least one binding agent which specifically binds to an extracellular target of leukocytes, and at least one binding agent which specifically binds to an intracellular target of leukocytes,
   wherein each of said binding agents comprises a detectable agent; and
(d) adding a third solution to said combination, wherein the added volume of said third solution is equal to or higher than the total volume of said combination to which the third solution is added.

In some instances, the method of the present invention is referred to herein as INCA method (Intracellular No Centrifuge Assay).

In one embodiment, the cellular composition containing the leukocytes to be stained is a biological fluid containing cells in suspension. In another embodiment, the cellular composition is selected from the group consisting of whole blood, bone marrow, peritoneal fluid, cephalic fluids, dissociated lymph nodes and other dissociated tissues. In a still further embodiment, the cellular composition is whole blood.

According to one embodiment, the combination obtained in step (a) of the method of the present invention is incubated for 5 to 20 minutes, in another embodiment for 10 to 15 minutes, prior to step (b). The one or more agent(s) that are capable of cross-linking intracellular proteins, lipoproteins and nucleic acids of leukocytes used in step (a) are, according to one embodiment, selected from the group consisting of formaldehyde, paraformaldehyde, and glutaraldehyde. In one embodiment, said agent(s) are contained in said combination in an amount of 0.5% to 2% (v/v) after addition of the first solution, and in said first solution in an amount of between 5% and 15% (v/v). In this context, it should be noted that step (a) of the method of the present invention is performed for fixing the cells contained in the cellular composition.

In one embodiment, the second solution added in step (b) of the method of the present invention, comprising one or more agent(s) that are capable of permeabilizing said leukocytes, lysing said red blood cells and neutralizing the cross-linking activity of said one or more agent(s) in said first solution, comprises (i) a detergent in an amount that is adapted to effect the lysis of substantially all red blood cells contained in the cellular composition, while the majority of leukocytes contained in the cellular composition are not lysed, and (ii) a neutralizing agent for neutralizing said agent(s) of step (a). According to one embodiment, said detergent contains a $C_{12}$-type alkane residue, according to another embodiment sodium N-lauroyl sarcosine, wherein the detergent is, according to one embodiment, contained in said second solution in an amount of 0.05% to 0.5% (w/v), according to another embodiment in an amount of 0.1% to 0.3% (w/v). Further, according to one embodiment, said neutralizing agent is a quaternary ammonium salt or an amine containing compound, according to another embodiment a compound, selected from the group consisting of ammonium chloride ($NH_4Cl$), glycine, tris(hydroxymethyl)aminomethane (Tris), and ethanolamine, wherein in a still further embodiment it is ammonium chloride. In one embodiment, said neutralizing agent is contained in said second solution in a concentration of 1 to 100 mM, in another embodiment in a concentration of 5 to 20 mM. In one embodiment, said second solution has a pH of 6.5 or lower. In another embodiment, the added volume of said second solution added in step (b) of the method of the present invention is between 1 and 10 times, in another embodiment between 4 and 8 times, and in a still further embodiment 6 times the total volume of the combination obtained in step (a). In this context, it should be noted that step (b) of the method of the present invention is performed for permeabilizing the leukocytes and lysing the red blood cells contained in the cellular composition, as well as for neutralizing the cross-linking activity of said one or more agent(s) in said first solution added in step (a).

Step (c) of the method of the present invention can be performed concurrently with step (b). In particular, the binding agents added in step (c) can already be contained in the second solution added in step (b). Alternatively, said binding agents can be added subsequently to addition of said second solution, wherein the extracellular and intracellular binding agents can be added either together as a binding agent cocktail, or separately. In one embodiment, the binding agents are molecular stains, in another embodiment antibodies, in a still further embodiment monoclonal antibodies. Further, the detectable agent comprised in said binding agents is not particularly limited, wherein suitable detectable agents are known in the art. According to one embodiment, said detectable agent is selected from the group consisting of a biotin, an enzyme, and a fluorescent moiety or compound, wherein, according to another embodiment, it is a fluorescent moiety or compound. In one embodiment, the combination obtained in step (c) is incubated for 15 to 60 minutes, in another embodiment for 30 to 45 minutes, prior to step (d). In this context, it should be noted that step (c) of the method of the present invention is performed for staining the leukocytes contained in the cellular composition.

The third solution added to said combination, i.e. to the combination obtained in step (c), in step (d) of the method of the present invention comprises according to one embodiment (i) a fixative, which in one embodiment is selected from the group consisting of formaldehyde, paraformaldehyde, and glutaraldehyde, and (ii) a detergent, containing, according to one embodiment, a $C_{12}$-type alkane residue, according to another embodiment sodium N-lauroyl sarcosine. In one embodiment, the above fixative is contained in the third solution in an amount of between 0.01% and 1% (v/v), and the above detergent in an amount of 0.01% to 0.5% (w/v). In another embodiment, the third solution further comprises a compound, selected from the group consisting of dextrane sulfate and Pluronic F-68, which is a polyoxyethylene-polyoxypropylene block copolymer with the linear formula $(C_3H_6O.C_2H_4O)_x$. Said further compound is, according to one embodiment, contained in the third solution in an amount of 0.1% (w/v).

In one embodiment, the method of the present invention does not contain any centrifugation step, e.g. for purifying said leukocytes, prior to step (d) or after step (b) or step (c), or any additional washing steps.

In another embodiment, the method of the present invention comprises one washing step after step (d), i.e. a step of centrifuging the cells, discarding the supernatant, and resuspending the cells in a suitable volume of the third solution used in step (d). This washing step can improve the signal-to-noise ratio which is particularly useful when working with rather dim stainings, and further concentrates the cells.

In another embodiment, the method of the present invention further comprises the step of detecting the bound binding agents on the leukocytes, according to one embodiment by flow cytometry.

In a further embodiment, all method steps of the method of the present invention are performed at room temperature.

In an even further embodiment, the method of the present invention is an automated method.

In another aspect, the present invention relates to a kit for performing the methods of the present invention, comprising a first solution, a second solution, and a third solution, wherein said first, second, and third solutions are as defined above.

In one particular embodiment, the kit of the present invention comprises:
(a) a first solution comprising formaldehyde in a concentration of between 5% and 15% (v/v);
(b) a second solution comprising
   (i) ammonium chloride ($NH_4Cl$) in a concentration of 1 to 100 mM, and
   (ii) sodium N-lauroyl sarcosine in a concentration of 0.05% to 0.5% (w/v); and
(c) a third solution comprising
   (i) formaldehyde in a concentration of between 0.01% and 1% (v/v), and
   (ii) sodium N-lauroyl sarcosine in a concentration of 0.01% to 0.5% (w/v).

In another embodiment, the kit of the present invention further comprises:
(a) at least one binding agent comprising a label that is detectable by flow cytometry, wherein said binding agent specifically binds to an extracellular target of leukocytes; and
(b) at least one binding agent comprising a label that is detectable by flow cytometry, wherein said binding agent specifically binds to an intracellular target of leukocytes;
wherein said extra- and intracellular binding agents are provided in separate tubes or as components of said second solution, and
wherein the binding agents and the respective detectable labels are as defined above.

In certain embodiments of the methods and kits of the present invention, the above first, second, and third solutions can further contain suitable additional components in suitable concentrations, such as buffer substances, e.g. 2-(N-morpholino)ethanesulfonic acid (MES) or phosphate-buffered saline (PBS); salts, e.g. sodium chloride; serum or serum components, e.g. bovine serum albumin; and preservatives, e.g. Proclin (5-chloro-2-methyl-4-isothiazolin-3-one).

The present invention advantageously provides an improved method for labeling intracellular and extracellular targets of leukocytes, as well as respective kits for performing said method. In particular, by choosing proper reagent compositions and dilution ratios with regard to each step of adding a solution, all time- and labor-consuming centrifugation steps can be omitted. This significantly speeds up the procedure and in addition protects the structure of the cells, so that e.g. light scatter properties are improved as compared to centrifuged cells. Moreover, a soft fixation step maintains the surface structures of the leukocytes intact, and remaining fixative is inactivated during permeabilization, so that the cells can be stained with extracellular binding agents even after fixation. Accordingly, the method of the present invention enables the use of cocktails comprising respective mixes of extra- and intracellular binding agents.

The present invention will now be further illustrated in the following examples without being limited thereto.

EXAMPLES

Example 1

Staining of Normal Human Whole Blood with a PE-Labeled Anti-ZAP-70 Antibody

Figure 1:
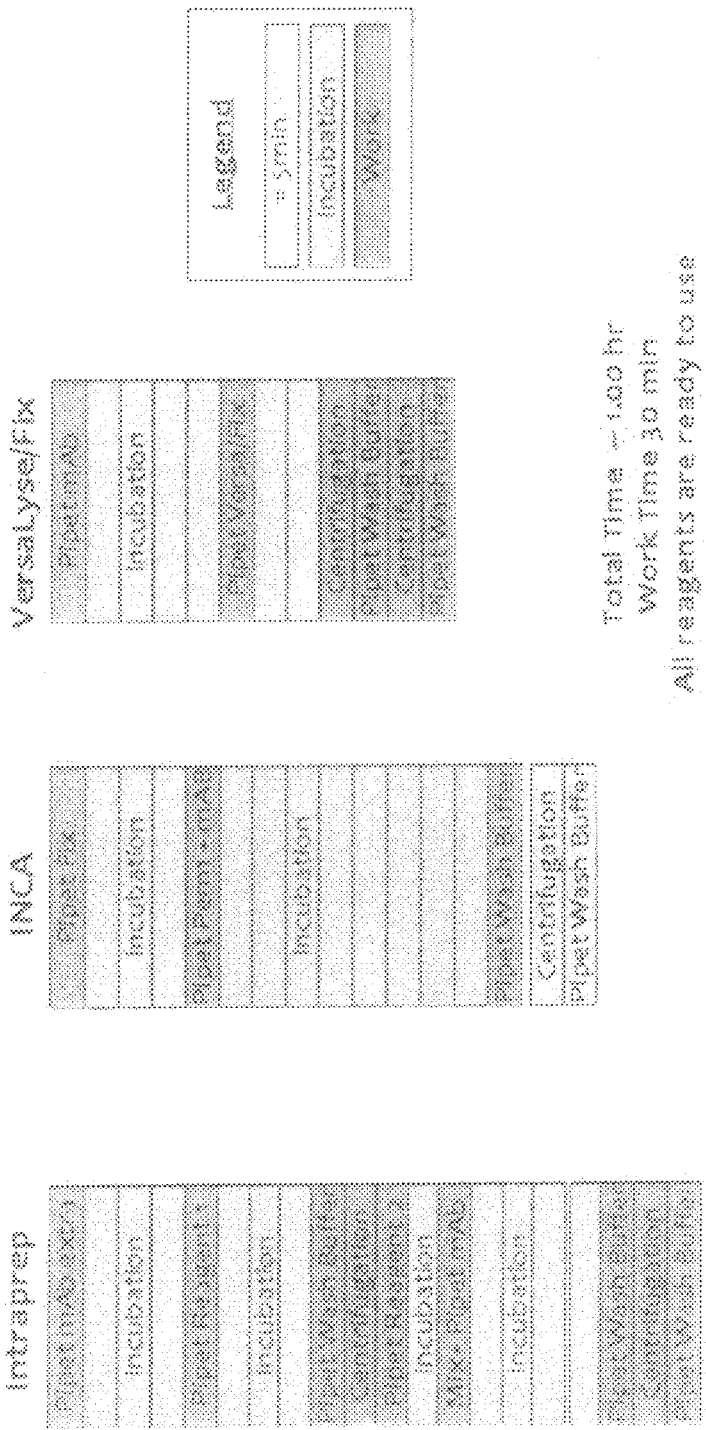
FIG. 1:
Workload comparison showing the amount of time and work needed to perform methods known in the art ("Intraprep" and "VersaLyse/Fix"), and the method of the present invention ("INCA"). Each bar represents 5 minutes of time; light gray bars show incubation time, dark gray bars show work time.
Figure 2:
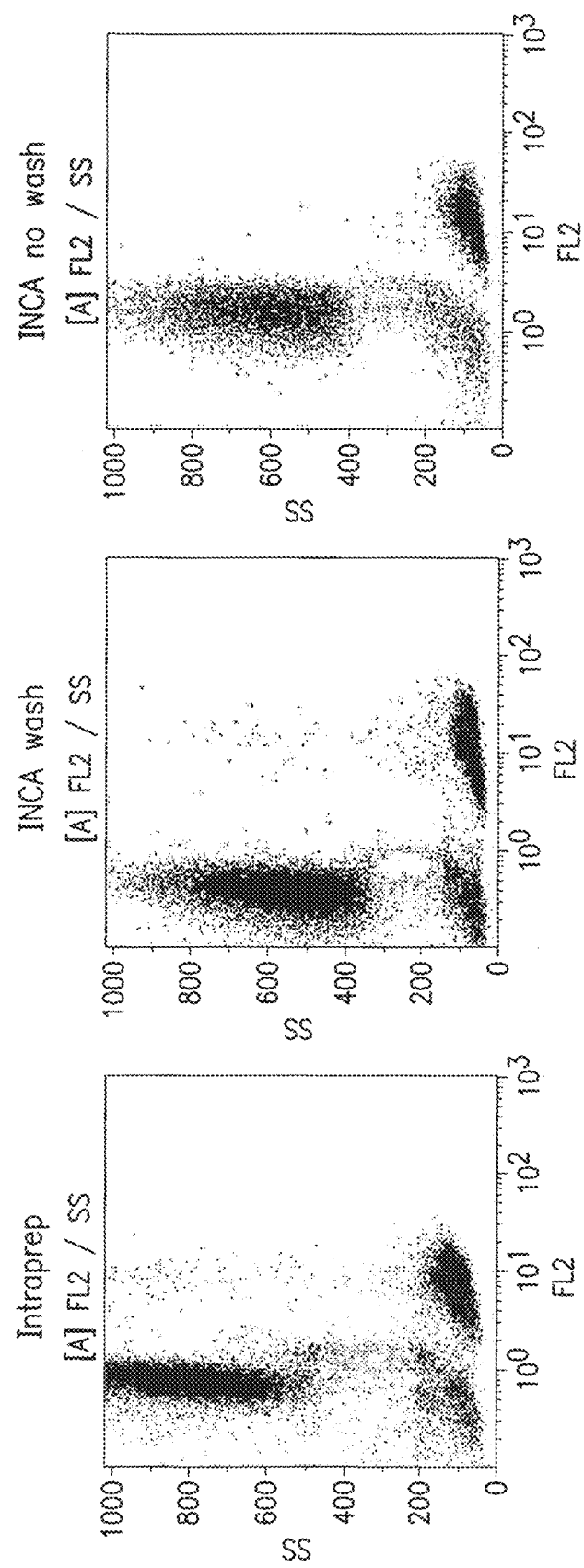
FIG. 2:
Staining of normal human whole with a PE-labeled anti-ZAP-70 antibody by a method known in the art ("Intraprep") and the method of the present invention, either with or without an additional washing step ("INCA wash" and "INCA no wash"). The dot plots show the intracellular staining with the antibody (FL2) versus sideward scatter.

Normal human whole blood was stained with a PE-labeled anti-ZAP-70 antibody by a method known in the art ("Intraprep") and the method of the present invention, either with or without an additional washing step ("INCA wash" and "INCA no wash") and subsequently analyzed by flow cytometry. FIG. 2 shows the respective stainings with the antibody (FL2) versus sideward scatter. The methods according to the present invention stained equal amounts of cells compared to the prior art method and showed a clearer separation from the unstained cells with an RMFI (relative mean fluorescence intensity, which is a measure for the signal-to-noise ration) of 30 (INCA wash) and 15 (INCA no wash).

Example 2

Figure 3:
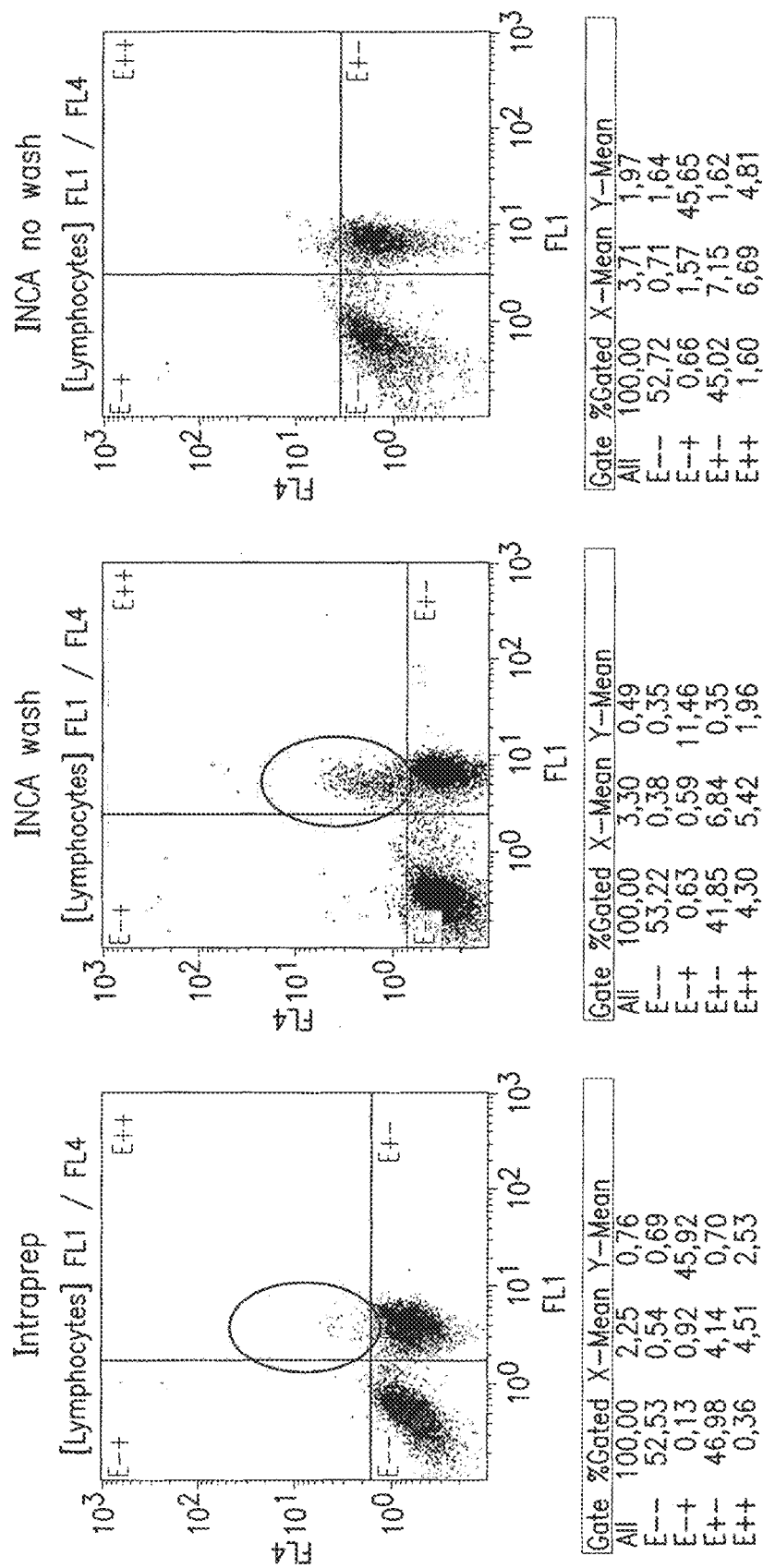
FIG. 3:
Staining of normal human whole blood with a FITC-labeled anti-CD4 antibody and an Alexa647-labeled anti-FoxP3 antibody by a method known in the art ("Intraprep") and the method of the present invention, either with or without an additional washing step ("INCA wash" and "INCA no wash"). The dot plots show surface staining with the anti-CD4 antibody (FL1) versus intracellular staining with the anti-FoxP3 antibody (FL4).

Staining of Normal Human Whole Blood with a FITC-Labeled Anti-CD4 Antibody and an Alexa647-Labeled Anti-FoxP3 Antibody Normal human whole blood was stained with a FITC-labeled anti-CD4 antibody and an Alexa647-labeled anti-FoxP3 antibody by a method known in the art ("Intraprep") and the method of the present invention, either with or without an additional washing step ("INCA wash" and "INCA no wash") and subsequently analyzed by flow cytometry. FIG. 3 shows the respective stainings with the anti-CD4 antibody (FL1) versus the intracellular stainings with the anti-FoxP3 antibody (FL4). The method known in the art stained only a small population of 0.36% of the cells, whereas the method of the present invention containing an additional washing step stained a substantial population of 4.3%.

Example 3

Staining of Normal Human Whole Blood with Various Intracellular Antibodies

Normal human whole blood was stained with various intracellular antibodies by a method known in the art ("Intraprep") and the method of the present invention, either with or without an additional washing step ("INCA wash" and "INCA no wash") as described above. Results of the respective stainings are shown in Table 1 below.

Results show that the method of the present invention provides at least comparable and in many cases superior stainings as a prior art method.

TABLE 1

| Quality of stainings | | | |
|---|---|---|---|
| Antibody | Intraprep | INCA wash | INCA no wash |
| CD125-PE | ++ | ++ | + |
| APO2.7-PE | + | ++ | ++ |
| DAP-12-PE | + | ++ | + |
| FoxP3-Alexa647 | − | ++ | − |
| Tia-1-PE | ++ | ++ | ++ |
| ZAP-70-PE | + | ++ | + |
| MPO-FITC | ++ | + | + |
| Lactoferrin-PE | ++ | + | + |
| CD79a-PE | + | ++ | ++ |
| IFNg-PE | ++ | ++ | + |
| TNFa-PE | ++ | ++ | + |
| CyclinA2-FITC | − | ++ | ++ |
| TdT-FITC | − | ++ | ++ |

++: best conditions
+: not optimal but staining works
−: no adequate staining

Example 4

Staining of Human Whole Blood without Washing Steps

In the following human whole blood samples were stained with Krome Orange-labeled anti-CD45 antibody, FITC-labeled anti-CD5 antibody, APC-labeled anti-CD19 antibody or a PE-labeled anti-ZAP-70 antibody. While the anti-CD19 antibody is directed against an extracellular epitope, the anti-ZAP-70 antibody is directed against intracellular epitope.

The following solutions were prepared and used within this example:
Solution 1: Formaldehyde 5.5% wt/vol
  $Na_2HPO_4$ 3 mM
  $NaH_2PO_4$ 3 mM
  NaCL 47 mM
  pH 6.8
Solution 2: NaCl 140 mM
  $NH_4Cl$ 10 mM MES 20 mM
NaLS 0.15%
BSA 0.5%
Proclin 300 0.05%
pH 6.3
Solution 3: Na2HPO4 11 mM
NaH2PO4 29 mM
NaCL 260 mM
NaLS 0.05%
Pluronic F68 0.1%
Formaldehyde 0.5% wt/vol
pH 7.2

In order to show whether intra- and extracellular epitopes can be stained using the present invention, a human whole blood sample (WBS) was processed in the following manner.

First, 50 μl of WBS were combined with 5 μl of solution 1 and incubated for 15 minutes. Then 300 μl of solution 2 were added, together with 10 μL of the labeled antibodies indicated. After 40 minutes of incuvation 3000 μl of solution 3 were added, and the mixture was vortexed.

The analysis of the above mixture was carried out using a flow cytometer device. It was shown that both intra- and extracellular epitopes were stained successfully. No difference could be seen when comparing the method outlined above having a washing step with a method as outlined above containing no washing step. Both method showed a sufficient staining.

Example 4a

Variations of Example 4

In order to find out whether the method of the present invention is a robust method which can be successfully used for many conditions, several variations of the solutions 1, 2, and 3 disclosed in Example 4 were tested.

In each case, 50 μl of WBS were combined with 5 μl of solution 1 (R1) and incubated for 15 minutes. Then 300 μl of solution 2 (R2) were added, together with 10 μl of each of the labeled antibodies indicated. After 30 minutes of incubation 3000 μl of solution 3 (R3) were added, and the mixture was vortexed.

As shown in Table 2 herein below, a setup was chosen where either the amount of solution 1 was varied or the concentrations of the ingredients of solution 2 was varied and/or the concentration of the ingredients of solution 3 was varied. In the various settings the concentration of several reagents was changed by + or −20% from the reference sample. The reference example is experiment No. 1 in Tables 2 and 3.

In the following table solution 1 is called R1, solution 2 is called R2, and solution 3 is called R3.

The above experimental settings were tested regarding their deviation of the signal to noise ratio in the detection of intra- and extracellular epitopes when compared to the reference experiment No. 1.

The following table 3 provides signal/noise values with regard to 3 intracellular targets and 2 extracellular targets. The conjugates used were Anti-MPO-FITC, anti-CD79a-PE, anti-CD3-ECD (IOTest3 cocktail PN IM3464U), and Anti-CD14-PC7 (PN A22331).

TABLE 3

| Signal to Noise ratios of the settings of Table 2 | | | | | |
|---|---|---|---|---|---|
| Sample no. | S/N MPO Mono | S/N MPO Granu | S/N CD79a | S/N CD3 | S/N CD14 |
| 1 | 18.6 | 32.2 | 32.9 | 54.3 | 354 |
| 2 | 14.1 | 21.4 | 27.3 | 52.5 | 348 |
| 3 | 15.6 | 26.3 | 25.2 | 54.4 | 347 |
| 4 | 30.4 | 31.7 | 34.9 | 51.5 | 325 |
| 5 | 25.8 | 34.8 | 37.9 | 55.7 | 339 |

As can be seen all experimental variations outlined in table 2 were working equally well regarding the signal to noise ratio. Accordingly, the present invention provides a robust system and method for detecting intra- and extracellular epitopes which works well over a great variety of buffer compositions including various concentrations of the buffer ingredients.

Example 5

Influence of an Additional Washing Step

In order to find out whether an additional washing step has any negative influence on the results obtained above, the conditions of Example 4 were varied insofar as a further washing step was added.

In particular, solutions 1, 2, and 3 as outlined in Example 4, above, were prepared and the following method for staining a human whole blood sample (WBS) with labeled antibodies was carried out.

First, 50 μl of WBS were combined with 5 μl of solution 1 and incubated for 15 minutes. Then 300 μl of solution 2 were added, together with 10 μL of each of the labeled antibodies indicated. After 40 minutes of incubation 3000 μl of solution 3 were added, and the mixture was vortexed. Finally, in addition to the above, the cell suspension was centrifuged (500 g, 5 min.), the supernatant was discarded, and the cell pellet is resuspended in 500 μL of the solution 3.

The results obtained using the above method did not differ from the results obtained in Example 4. Thus, an additional

TABLE 2

| Variations of solutions 1, 2, and 3 | | | | | | | | | | |
|---|---|---|---|---|---|---|---|---|---|---|
| | FIX | PERM (R2) | | | | | | | WASH (R3) | |
| No. | (R1) μL | MES (mM) | NaCl (mM) | NH4CL (mM) | BSA (%) | NALS (%) | Proclin (%) | pH | FA (%) | LS (%) | F68 (%) |
| 1 | 5 | 10 | 140 | 10 | 0.5 | 0.15 | 0.05 | 6.3 | 0.5 | 0.05 | 0.1 |
| 2 | 6 | 12 | 168 | 12 | 0.6 | 0.18 | 0.06 | 6.5 | 0.6 | 0.06 | 0.12 |
| 3 | 6 | 12 | 112 | 8 | 0.4 | 0.18 | 0.04 | 6.1 | 0.6 | 0.04 | 0.12 |
| 4 | 6 | 12 | 168 | 8 | 0.4 | 0.12 | 0.06 | 6.1 | 0.4 | 0.06 | 0.08 |
| 5 | 4 | 12 | 168 | 12 | 0.4 | 0.12 | 0.04 | 6.5 | 0.4 | 0.04 | 0.12 | washing step does not have any essential influence on the result achieved. This again shows that the system and method according to the present invention is robust over various parameters.

Example 6

Influence of pH Variations

In order to show the influence of differences in the pH value the solutions used on the outcome of the system and method according to the present invention, an experimental setup was chosen, wherein the pH of solution 2 was varied.

Regarding the experimental setup, the method for staining a human whole blood sample as outlined in Example 4 was carried out using the variations of solutions 1, 2, and 3 as outline for reference experiment No. 1 given in Table 2 of Example 4a. In particular, it was determined as to whether the signal to noise ratio is drastically influenced by a variation of the pH of solution 2. The staining of the human whole blood sample was done by using a PE-labeled anti-ZAP-70 antibody.

As can be taken from Table 4, below, the signal to noise ratio did not differ significantly when the pH of solution 2 was varied from pH 6.00 to pH 6.91.

TABLE 4

Variation of the pH of solution 2

| pH LYSE | | | | | | | |
|---|---|---|---|---|---|---|---|
| 6.00 | 6.12 | 6.26 | 6.35 | 6.46 | 6.60 | 6.74 | 6.91 |
| RMFI 34.3 | 33.4 | 35.9 | 35.9 | 33.6 | 30.9 | 28.0 | 26.9 |

What is claimed is:

1. A method for labeling a marker of leukocytes, comprising the steps of:
   (a) forming a first combination including:
   (i) a cellular composition comprising leukocytes, and
   (ii) a cross-linking agent that is formaldehyde, wherein the concentration of said cross-linking agent in said first combination is 0.5% to 2% (v/v);
   (b) forming a second combination including:
   (i) said first combination,
   (ii) a solution comprising a permeabilizing agent that permeabilizes said leukocytes and a neutralizing agent comprising a mixture of sodium chloride and (NaCl) and ammonium chloride ($NH_4Cl$) and optionally glycine, tris(hydroxymethyl)aminomethane (Tris), ethanolamine, or a mixture thereof, in a concentration of 1 to 100 mM in said solution, wherein said neutralizing agent neutralizes the cross-linking activity of said cross-linking agent and a pH of said solution is in a range of 6.0 and 6.6; and
   (iii) a binding agent that binds a marker of said leukocyte, wherein the binding agent comprises a detectable agent,
   wherein no centrifugation is performed between step (a) and step (b) and the permeabilizing agent is added in an amount sufficient so as to permeabilize said leukocytes, and so as to lyse said red blood cells to effect the lysis of substantially all red blood cells contained in the cellular composition, while the majority of leukocytes contained in the cellular composition are not lysed.

2. The method according to claim 1, wherein the concentration of said neutralizing agent in said solution is 5 to 20 mM.

3. The method according to claim 1, wherein the volume of said solution is 1 to 10 times the volume of said first combination.

4. The method according to claim 3, wherein the volume of said solution is 4 to 8 times the volume of said first combination.

5. The method according to claim 3, wherein the volume of said solution is six times the volume of said first combination.

6. The method of claim 1, wherein said binding agent is in a binding agent cocktail that includes extracellular and intracellular binding agents.

7. The method according to claim 1, wherein said permeabilizing agent contains a $C_{12}$-type alkane residue.

8. The method according to claim 1, wherein the binding agent comprises a first antibody binding agent which specifically binds to an extracellular target of leukocytes, and a second antibody binding agent which specifically binds to an intracellular target of leukocytes, wherein said first antibody binding agent comprises a first detectable agent and said second antibody binding agent comprises a second detectable agent.

9. A method for labeling a marker of leukocytes, comprising the steps of:
   (a) forming a first combination including:
   (i) a cellular composition comprising leukocytes, and
   (ii) a cross-linking agent selected from the group consisting of formaldehyde, paraformaldehyde, and glutaraldehyde, wherein the concentration of said cross-linking agent in said first combination is 0.5% to 2% (v/v);
   (b) forming a second combination including:
   (i) said first combination,
   (ii) a permeabilizing agent that permeabilizes said leukocytes,
   (iii) a neutralizing agent comprising a mixture of ammonium chloride ($NH_4Cl$) and sodium chloride and optionally, glycine, tris(hydroxymethyl)aminomethane (Tris), and ethanolamine, wherein said neutralizing agent has a concentration of 1 to 100 mM in said mixture and neutralizes the cross-linking activity of said cross-linking agent; and
   (iv) a binding agent that binds a marker of said leukocytes, wherein the binding agent comprises a detectable agent, wherein said binding agent is added after step (a) and no centrifugation is performed between step (a) and step (b), wherein a pH of the neutralizing agent mixture is in a range of 6.0 and 6.6.

10. The method according to claim 9, wherein said binding agent binds an intracellular target of said leukocytes.

11. The method according to claim 9, wherein said binding agent is in a binding agent cocktail that includes extracellular and intracellular binding agents.

12. A method for preparing leukocytes for staining, comprising the steps of:
   (a) forming a first combination including:
   (i) a cellular composition comprising leukocytes, and
   (ii) a cross-linking agent selected from the group consisting of formaldehyde, paraformaldehyde, and glutaraldehyde, wherein the concentration of said cross-linking agent in said first combination is 0.5% to 2% (v/v);
   (b) forming a second combination including:
   (i) said first combination, and
   (ii) a solution comprising a permeabilizing agent containing a $C_{12}$-type alkane residue that permeabilizes said leukocytes and a neutralizing agent comprising a mixture of sodium chloride and (NaCl) and ammonium chloride ($NH_4Cl$) and optionally glycine, tris(hydroxymethyl)aminomethane (Tris), ethanolamine, or a mixture thereof, wherein said neutralizing agent has a concentration of 1 to 100 mM in said mixture and neutralizes the cross-linking activity of said cross-linking agent and a pH of said solution is in a range of 6.0 and 6.6, wherein no centrifugation is performed between step (a) and step (b) and the permeabilizing agent is added in an amount sufficient to permeabilize said leukocytes, and so as to lyse said red blood cells, wherein said permeabilizing agent is in an amount adapted to effect the lysis of substantially all red blood cells contained in the cellular composition, while the majority of leukocytes contained in the cellular composition are not lysed.

13. The method according to claim 12, wherein said permeabilizing agent is N-Lauroyl sarcosine.

14. The method according to claim 12, wherein the concentration of said neutralizing agent in said solution is 5 to 20 mM.

15. The method according to claim 12, wherein the volume of said solution is 1 to 10 times the volume of said first combination.

\* \* \* \* \*